(12) United States Patent
McKay et al.

(10) Patent No.: US 8,383,586 B2
(45) Date of Patent: Feb. 26, 2013

(54) COMPOSITIONS AND METHODS FOR SOFT TISSUE REPAIR

(75) Inventors: William F. McKay, Memphis, TN (US); Susan J. Drapeau, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 315 days.

(21) Appl. No.: 11/624,450

(22) Filed: Jan. 18, 2007

(65) Prior Publication Data

US 2008/0175911 A1 Jul. 24, 2008

(51) Int. Cl.
*A61K 38/18* (2006.01)
*A61K 38/00* (2006.01)
*A61K 38/16* (2006.01)

(52) U.S. Cl. ........ 514/8.9; 514/16.5; 514/7.6; 514/21.2; 514/1.1

(58) Field of Classification Search .................. None
See application file for complete search history.

(56) References Cited

U.S. PATENT DOCUMENTS

| | | | |
|---|---|---|---|
| 5,143,724 A * | 9/1992 | Leshchiner et al. | 424/78.08 |
| 6,428,576 B1 * | 8/2002 | Haldimann | 623/17.16 |
| 8,048,857 B2 * | 11/2011 | McKay et al. | 514/16.7 |
| 2002/0032155 A1 | 3/2002 | Ferree | |
| 2002/0116069 A1 | 8/2002 | Urry | |
| 2002/0176893 A1 | 11/2002 | Wironen et al. | |
| 2004/0220101 A1 | 11/2004 | Ferree | |
| 2004/0220102 A1 | 11/2004 | Ferree | |
| 2005/0069571 A1 | 3/2005 | Slivka et al. | |
| 2005/0142163 A1 | 6/2005 | Hunter et al. | |
| 2005/0149175 A1 | 7/2005 | Hunter et al. | |
| 2005/0186247 A1 | 8/2005 | Hunter et al. | |
| 2008/0004703 A1 * | 1/2008 | Trieu et al. | 623/17.16 |

OTHER PUBLICATIONS

Phillips, A., J Pharm Pharmacology 53: 1169-1174, 2001.*
Ling et al. 2002. Clinical and Experimental Allergy 32:175-178.*
DeFail et al. 2006. Biomaterials 27:1573-1585.*
Lee et al. 2006. J Biomed Mater Res A 76:530-9.*
http://dictionary.reference.com/browse/granule, pp. 1-3 included, downloaded Sep. 12, 2008.*
Beck et al. 1993. J. Clin Invest. 92:2841-2849.*
Walsh et al., "In vivo growth factor treatment of degenerated intervertebral discs," Spine, 2004 29(2), pp. 156-163.
Chujo et al., "Effects of growth differentiation factor-5 on the inervertebral disc—in vitro bovine study and in vivo rabbit disc degeneration model study," Spine, 2006, 31(25), pp. 2909-2917.
Y.T. Konttinen, et al., "Transforming and epidermal growth factors in degenerated intervertebral discs," The Journal of Bone & Joint Surgery, vol. 81B ( No. 6), p. 1058-1063, (Nov. 1999).
Andreas G. Nerlich, et al., "Expression of fibronectin and TGF-beta1 mRNA and protein suggest altered regulation of extracellular matrix in degenerated disc tissue", European Spine Journal, vol. 14(1), p. 17-26, Feb. 2005.

* cited by examiner

*Primary Examiner* — Shulamith H Shafer
(74) *Attorney, Agent, or Firm* — Sorell Lenna & Schmidt LLP (57) ABSTRACT

Methods and compositions for treating soft tissue defects are provided. The composition, which is injectable directly into the tissue adjacent to the defect, comprises a fibrosis inducing factor in a carrier. The method includes preparing the composition comprising a fibrosis inducing factor in a carrier and delivering the composition into the tissue adjacent to the defect. Alternatively, a carrier matrix may be disposed in or near the defect, a pump capable of delivering an effective amount of a fibrosis inducing factor may be provided, and the pump is fluidly connected to the carrier matrix.

11 Claims, 7 Drawing Sheets

COMPOSITIONS AND METHODS FOR SOFT TISSUE REPAIR

FIELD OF THE INVENTION

The present invention relates to methods for treatment of soft tissues. More particularly, the present invention discloses methods and related compositions for administering a fibrosis inducing factor to treat various soft tissue defects.

BACKGROUND OF THE INVENTION

Soft tissue injuries are very common. Knee pain, for example, is a complaint in up to 20% of the general adult population, accounting for almost 3 million outpatient and emergency department visits per year. Trauma to the knee is the second most common occupational accident. In National Collegiate Athletic Association (NCAA) football, 1 major knee injury occurs per team every year. Sports-related activity accounts for approximately 60% of knee injuries producing ligamentous laxity.

Another common complaint associated with defects in soft tissue is spinal pain which has been estimated to exist in as much as 66% of the general population. Beyond the substantial discomfort that back pain inflicts upon individuals, spine-related pain also incurs heavy societal costs. For example, as many as one million spinal surgeries, and as many as five million interventional procedures, are estimated to be performed in the United States each year. Well beyond the purely medical and psychological burdens imposed by such procedures, the subsequent societal costs related to productivity, disability compensation and lost taxes are substantial.

Currently, there are no effective alternatives for treatment of soft tissue injuries. Although there are many therapeutic medications that are commonly used in the management of soft-tissue injuries, very few medications have strong evidence of a consistent therapeutic effect. On the other hand, surgical intervention is expensive, results in long recovery times, and may cause patients to experience subsequent pain levels to a degree that is equal to, or even exceeding, their pre-surgery levels.

Accordingly, it is desirable to improve the existing methods of treatment of soft tissue injuries. Furthermore, there is a need for minimally invasive methods to halt or reverse degeneration of soft tissues during the early stages of the disease.

SUMMARY OF THE INVENTION

In one aspect, a composition for treatment of defects in soft tissue is provided. The composition comprises a fibrosis inducing factor and a carrier and is injectable directly into the soft tissue adjacent to the defects.

The composition is suitable for treatment of soft tissues that include, but are not limited, muscles, tendons, ligaments, fibrous tissues, fibrocartilage, annulus fibrosus, cartilage, connective tissue, fat, blood vessels, nerves, and synovial tissues.

Suitable fibrosis inducing factors include, but are not limited to, transforming growth factor-beta ("TGFβ"), TGFβ1, TGFβ2; platelet derived growth factor ("PDGF"); fibroblast growth factor ("FGF"); cartilage derived morphogenic protein ("CDMP"); growth and differentiation factor ("GDF"); bone morphogenetic protein ("BMP"); antibodies to TGFβ3, interferon alpha and interferon alpha 2b; RNA interference agent ("RNAi agent") to TGFβ3, interferon alpha and interferon alpha 2b and combinations thereof. In some embodiments, the fibrosis inducing factor may be included in a sustained release composition. It may, for example, be encapsulated into microspheres or incorporated into semipermeable matrices of biodegradable solid polymers.

The carrier may be in the form of a biocompatible fluid, a gel, or a slurry. The slurry may be formed by mixing a biocompatible fluid with a synthetic or a natural polymer.

In another aspect, a method of treatment for defects in soft tissues is provided. The method comprises preparing a composition comprising a fibrosis inducing factor in a carrier and delivering the composition into the soft tissues adjacent to the defects. The composition may be delivered to the soft tissue by injection or by using either an internal or external pump. The composition may be delivered from the pump via a catheter.

In yet another aspect, a method of treatment of a defect in soft tissue is provided. The method comprises disposing a carrier matrix in or near the defect, providing a pump capable of delivering an effective amount of a fibrosis inducing factor, and fluidly connecting the pump to the carrier matrix. The pump may either be an external or an internal pump, which may be fluidly connected to the carrier matrices via a catheter. Suitable examples of carrier matrix include gels and slurries comprising biocompatible fluids and natural or synthetic polymers.

DETAILED DESCRIPTION

A composition is provided for treatment of soft tissue defects, which is injectable into tissue surrounding the defect. The term "soft tissue" refers to tissues that connect, support, or surround other structures and organs of the body. Such tissues include, but are not limited to, muscles, tendons, ligaments, fibrous tissues, connective tissues, fibrocartilage, cartilage, fat, blood vessels, nerves, and synovial tissues. The composition comprises a fibrosis-inducing factor and a carrier.

The term "fibrosis inducing factor" means a substance that induces, increases, or accelerates formation of fibrous connective tissue. Examples of fibrosis inducing factors include, but are not limited to, transforming growth factor-beta ("TGFβ") such as TGFβ1 and TGFβ2; platelet derived growth factor ("PDGF"), fibroblast growth factor ("FGF"); cartilage derived morphogenetic protein ("CDMP"); growth and differentiation factor ("GDF"); bone morphogenetic protein ("BMP"); tumor necrosis factor alpha ("TNFa"), interleukin-1 ("IL-1") such as IL-1a and IL-1β; Interleukin-6 ("IL-6"); NFk-beta transcription factors; Matrix Metaloproteases (MMPs) and combination thereof.

Additionally, the term "fibrosis inducing factor" includes substances that prevent formation of or that block substances responsible for reducing or controlling scar formation. For example, studies have shown that TGFβ3 may have an important role in controlling the fibrotic effect of TGFβ1, thus reducing scar formation. (Murata et al. (1997) J Invest Dermatol., Shah et al. (1995) J Cell Sci.) Cytokines, especially interferon alpha and interferon alpha 2b may also reduce scar formation. (Komarcevic (2002) Med Pregl.). Accordingly, the term "fibrosis inducing factor" includes substances that deactivate or block the effects of TGFβ3 or interferon alpha such as antibodies. This type of antibodies is available, for example, from Sigma-Aldrich, St. Louis, Mo. It also includes RNA interference agent ("RNAi agent") that may be employed to block or decrease production of TGFβ3, interferon alpha or any other substances that reduce or prevent scar formation.

"RNAi agent" refers to ribonucleic acid sequences, modified ribonucleic acid sequences, or DNA sequences encoding said ribonucleic acid sequences, which cause RNA interference and thus decrease expression of the target gene. RNAi agent includes, without limitations, antisense oligodeoxynucleotides, shRNAs, siRNAs, miRNAs, and DNA-RNA hybrids. RNAi agent synthesis and their use is well known in the art. (see e.g. Caniggia (1999) J Clin Invest., Matveeva (2000) Nucleic Acid Res; Elbashir et al. (2001) EMBO J.). Various web-based programs exist for designing and optimizing RNAi agents (see e.g., siDESIGN Center at Dharmacon; BLOCK-iT RNAi Designer at Invitrogen; RNAi Design, OligoAnalyzer at Integrated DNA Technologies; and siRNA Target Finder at Genscript). Finally, many treatises on recombinant DNA methods of synthesis and introduction into target cells have been published (see e.g., Davis. et al., Basic Methods in Molecular Biology, Elsevier (1986), and Ausubel, et al., Current Protocols in Molecular Biology, Wiley Interscience (1988); Sambrook and Russel, Molecular Cloning: A laboratory Manual (3$^{rd}$ Edition), Cold Springs Harbor, Press, NY, 2000.)

In one specific embodiment, the fibrosis inducing factor comprises TGFβ1. TGFβ1 is synthesized as a 391-amino-acid precursor molecule that is proteolytically cleaved to yield peptide fragments and a 112-amino-acid subunit. Active TGFβ1 is a 25-KDa homodimeric protein composed of two subunits linked by a disulfide bond. TGFβ1 is secreted in an inactive, i.e., latent form and is stored at the cell surface and in the extracellular matrix. In response to stimulation, inactive TGFβ1 at these sites becomes activated. TGFβ1 binds at least three membrane proteins, known as receptor types 1, 2, and 3, that exist in virtually all types of cells. The type 1 and 2 receptors are transmembrane serine-threonine kinases that interact with one another and facilitate each other's signaling. The type 3 receptor, betaglycan, is a membrane-anchored proteoglycan that has no signaling structure but presents TGFβ1 to other receptors. The type 1 receptor mediates the effect of TGFβ1 on the synthesis and deposition of extracellular matrix and the type 2 receptor mediates the effect of TGFβ1 on cell growth and proliferation.

TGFβ1 has been implicated in the causation of fibrotic conditions. During normal tissue repair, TGFβ1 production is increased to stimulate the process of repair. TGFβ1 induces deposition of the extracellular matrix by simultaneously stimulating cells to increase the synthesis of most matrix proteins, decrease the production of matrix-degrading proteases, increase the production of protease inhibitors, modulate the expression of integrins to increase cellular adhesion to the matrix, and promote the fibroblast survival rate. When repair is complete, TGFβ1 production is reduced. If not reduced following normal tissue repair, the increased TGFβ1 overproduction can result in the development of excess extracellular matrix accumulation and fibrotic conditions. Thus, repeated tissue injury or a defect in TGFβ1 regulation leading to sustained TGFβ1 production results in excess accumulation of extracellular matrix. Both allogenic and xenogenic TGFβ1 is available commercially from different manufactures such as, for example, Promega Corp. (Madison, Wis.) or Sigma-Aldrich (St. Louis, Mich.). Alternatively, TGFβ1 can be prepared in accordance with U.S. Pat. No. 4,886,747.

The fibrosis inducing factor may be included in a sustained release composition. It may, for example, be entrapped in a microsphere prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980). Preferably, the microspheres have a diameter between about 1 to 250 microns.

Alternatively, the fibrosis inducing factor may be incorporated into semipermeable matrices of biodegradable solid polymers. The matrices may be in the form of shaped articles, e.g., films, rods, or pellets. Suitable materials for sustained-release matrices include, but are not limited to, poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, or combinations thereof. Polymers such as ethylene-vinyl acetate and lactic acid-glycolic acid enable release of molecules for over 100 days. Processes for preparing sustained-release compositions are well known and are described, for example, in U.S. Pat. No. 6,479,065 among others.

Although the microspheres or biodegradable matrices containing the fibrosis inducing factor may be injected into soft tissue on their own, a carrier may be provided to facilitate the delivery of the fibrosis inducing factor to the tissue. Example flowable carriers include, but are not limited to, a biocompatible fluid, a gel, or a slurry. In some embodiments, the carrier may set up or partially set up upon delivery. Preparation of in-situ curable matrix is known in the art. See e.g., U.S. Pat. Nos. 6,703,041, 6,312,725, and 7,135,140, incorporated herein by reference in their entirety.

A person of ordinary skill in the art would undoubtedly realize that both slurry and gel formulations will provide for a non-immediate release of the fibrosis inducing factor even in the embodiments where the fibrosis inducing factor is not in a sustained release formulation. In the preferred embodiments, the concentration of the fibrosis inducing factor in the carrier is between approximately 0.1 and 10.0 mg/mL, and more preferably between about 2 and 6 mg/mL.

Suitable biocompatible fluids include, but are not limited to, water, saline solution, buffered solutions, blood, blood with thrombin, bone marrow aspirant, concentrated plasma, concentrated or fractioned blood, concentrated or fractioned bone marrow, glycerol or any combination thereof. In the preferred embodiments, the biocompatible fluid is a buffered solution.

To form a slurry, a natural or a synthetic polymer may be mixed with the biocompatible fluid. The polymer may facilitate sustained release of the fibrosis inducing factor into the tissue to enhance efficacy of the treatment and to reduce the need for repeated administration. Preferably, the volume ratio of the biocompatible fluid to the dry polymer is between approximately 1:0.5, i.e. lower viscosities slurries, to 1:50, i.e. higher viscosity slurries. More preferably, the volume ratio of the biocompatible fluid to the dry polymer ranges between about 1:2 to 1:5. A 1:2 ratio of biocompatible fluid to dry carrier indicates that 1 ml of biocompatible fluid is used for approximately 2 cc of dry polymer.

Natural polymer examples include, but are not limited to, collagen, gelatin, chitosan, carboxymethylcellulose, hyaluronic acid, elastin, silk, glycosaminoglycans, polysaccharides, proteoglycans, peptides, polypeptides, or any combinations thereof.

Synthetic polymer examples include, but are not limited to, poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, polyphosphoesters, polyanhydrides, polyester-anhydrides, polyurethane-esters, polyphosphazines, polycaprolactones, polytrimethylene carbonates, polydioxanones, polyamide-esters, polyketals, polyacetals, glycosaminoglycans, polyethylene-vinyl acetates, silicones, polyurethanes, polypropylene fumarates, polydesaminotyrosine carbonates, polydesaminotyrosine arylates, polydesaminotyrosine ester carbonates, polydesaminotyrosine ester arylates, polyethylene oxides, polyorthocarbonates, polycarbonates, or copolymers or physical blends thereof or combinations thereof.

Additionally, hydrogels may be used as a carrier for delivery of the fibrosis inducing factors to the tissue. Suitable examples of hydrogels include, without limitations, polysaccharides, proteins, polyphosphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), sulphonated polymers, poly(N-vinyl-2-pyrrolidone), polyethylene glycol, polyethyleneoxide, poly(2-hydroxy ethyl methacrylate), copolymers of acrylates with N-vinyl pyrrolidone, N-vinyl lactams, and combinations thereof.

In another aspect, a method of treatment of defects in soft tissues is provided. Such method comprises preparing a composition comprising a fibrosis inducing factor in a carrier as described above and delivering the composition into the tissues adjacent to the defect. Injecting the composition directly into the tissue adjacent to a defect may be preferable for a number of reasons. First, it targets healthy tissue instead of the injured tissue. The healthy tissue may be capable of repairing the defect faster and more efficiently than the injured tissue because it still contains the desired responding cell population as opposed to the cells within the injured tissue defect. Second, it ensures more even distribution and residence time of the fibrosis inducing factor throughout the tissue because it is held within the interstitial spaces of healthy tissue as opposed to an open chemically hostile environment within the injured tissue defect. Third, the fibrosis inducing factor may be delivered using less carrier material when administered into the tissue adjacent to the defect because the carrier is not having to also provide the function of "space maintenance" if it were placed within the injured tissue defect. Finally, localized delivery aids in reducing the dose of the fibrosis inducing factor required for successful treatment.

In one embodiment, the composition comprising the fibrosis inducing factor and the carrier organic material can be delivered by an injection. Between 10 uL and 5 mL of the composition may be injected. Preferably, the injection volume is between 0.2 mL and 3 mL, and most preferably between 0.2 mL and 1 mL. The total dose of the fibrosis inducing factor administered to the patient may range between 0.001 and 60 mg depending on the severity of the soft tissue defect or patient's health. Preferably, the dose of the fibrosis inducing factor is between approximately 10 and 40 mg. For example, patients with known co-morbidities such as smokers, diabetics, and those on steroids may require a higher dose of the fibrosis inducing factor. The fibrosis inducing factor may be delivered from the composition over a period of time ranging from several minutes to several months.

Different delivery devices are suitable for this method of administration, suitable non-limiting examples being a needle or a cannula connected to a reservoir containing the composition such as a syringe. Since it is desirable to prevent additional trauma to the tissues, the delivery device should have a relatively small cross-section, such as, for example, 8G or smaller, or more preferably 12G or smaller. Accordingly, it may be beneficial, although not necessary, if the composition in this embodiment is sufficiently fluid to be delivered by this mode of administration.

Figure 1:
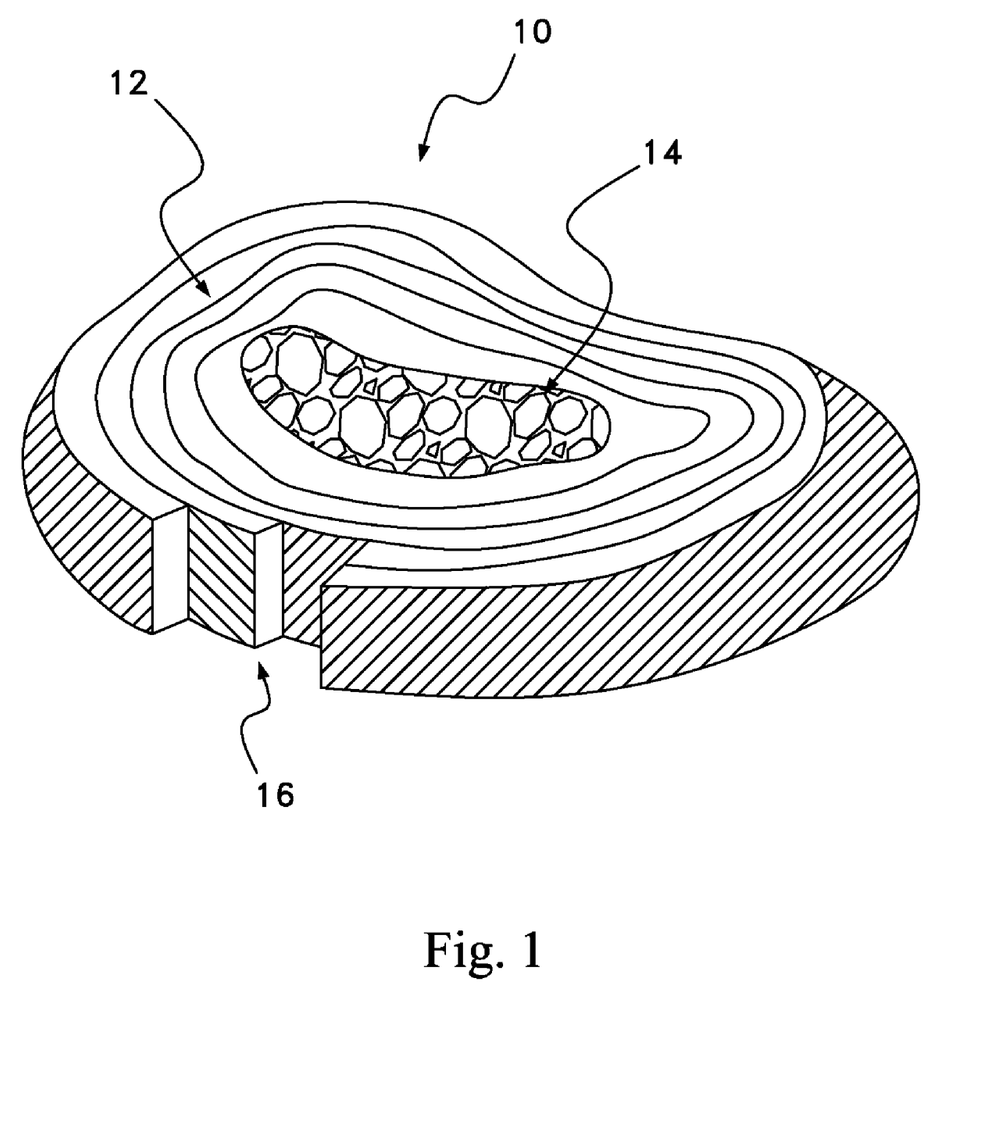
FIG. 1 is a cross-sectional view of an intervertebral disc.

For purposes of illustration only, FIG. 1a illustrates an intervertebral disc 10 which is made up of two components: the annulus fibrosus 12 and the nucleus pulposus 14. The nucleus pulposus 14 is the inner gelatinous material surrounded by the annulus fibrosus. It distributes mechanical loads placed upon the disc 10, while the annulus fibrosus 12 provides structural integrity and constrains the nucleus pulposus 14 to a specific spinal region. The annulus fibrosus 12 is designed with fibrocartilaginous and fibrous tissue arranged in concentric layers called laminae 16. As one moves, from the nucleus pulposus to the periphery, the annulus fibrosus tissue becomes more dense, stronger, less elastic, less fluid, and more ligamentous until reaching the outermost layers. There, the tissue actually becomes a tough, capsular ligament.

Figure 2A:
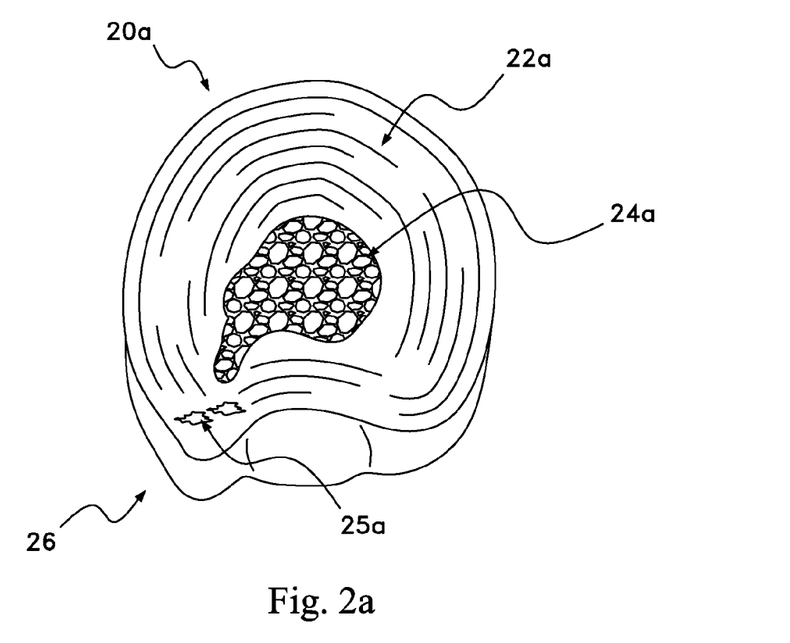
FIG. 2a is a cross-sectional view of a herniated intervertebral disc.
Figure 2B:
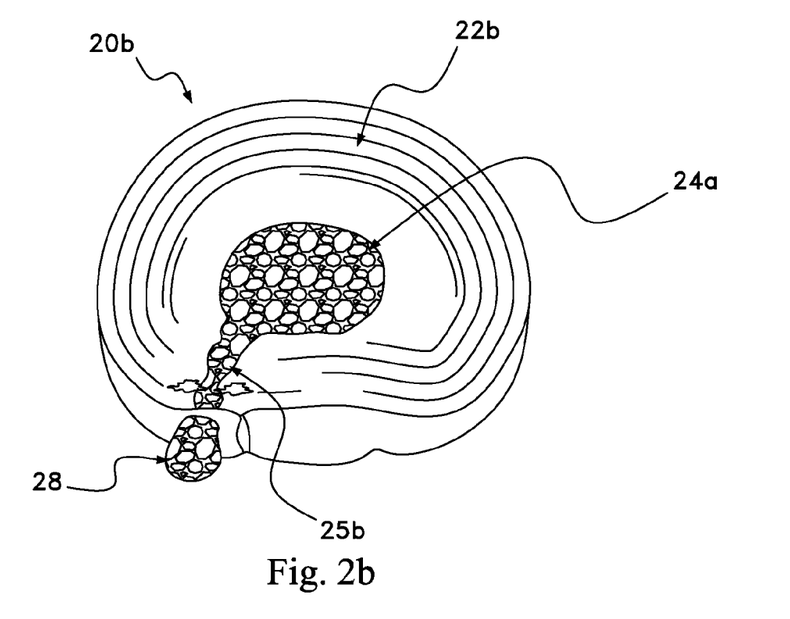
FIG. 2b is a cross-sectional view of a ruptured intervertebral disc.

The annulus fibrosus can become weaker with age, and may begin to tear. As shown in FIG. 2a, defects 25a in annulus fibrosus 22a allow bulging 26, or, as shown in FIG. 2b, complete rupturing 28 of the annulus fibrosus 22a and 22b. The herniated 20a or ruptured 20b disc compresses the spinal canal and exerts pressure on the nerve roots that pass through the disc 20a, 20b causing lower back pain. In addition, the nucleus pulposus 24a, 24b contains significant amounts of substances capable of exciting, or increasing the excitability of, sensory nerves such as prostaglandin E, histamine-like substances, lactic acid and polypeptide amines. These substances may escape through the annular tears 28, increasing the lower back pain or resulting in radiating leg pain.

Figure 3:
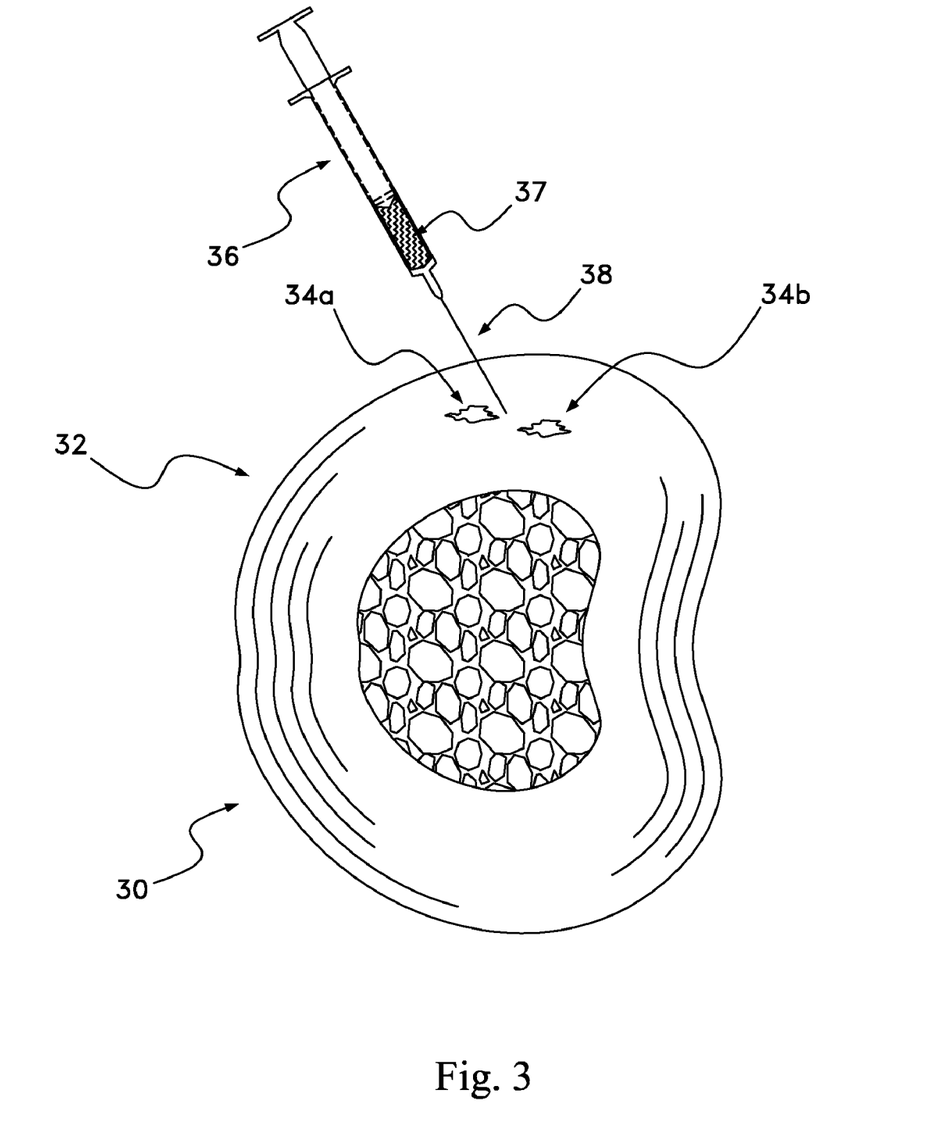
FIG. 3 and FIG. 4 illustrate administering a composition into tissue of the annulus fibrous according to one embodiment.

FIG. 3 shows an intervertebral disc 30 having tears 34a and 34b in annulus fibrosis 32. The composition 37 is delivered from a syringe 36 through a needle 38 into tissue adjacent to tears 34a and 34b. The composition may be injected into the tissue within about 5 cm of the defect. Preferably, it is injected within 2 cm of the defect, and more preferably within 1 cm of the defect.

In the preferred embodiment, the composition comprises a TGF-beta-1 entrapped in microspheres which are delivered using a PEG as a carrier. Preferably, 1 ml of PEG is injected into a soft tissue in a flowable form. Preferably, PEG is prepared in such a way that it sets up in-situ within about 15 to 30 seconds after the injection. The TGF-beta-1 is released over approximately 60 days at a rate of about 0.5 mg per day. This procedure may be repeated as necessary.

In another embodiment, the composition as described above may be delivered to the target site using a pump disposed either within or outside a patient. Preferably, approximately 1 to 5 mg of the fibrosis inducing factor is delivered over a 1 week to 24 months period, and preferably over about 1 month to 3 months period. Since the fibrosis inducing factors are often proteins, they are subject to degradation from acids, enzymes and other compounds that leach from the tissue surrounding the target site. Accordingly, use of a pump may be preferable when administration of the fibrosis inducing factor over a extended period of time is required. This method will ensure that the fibrosis inducing factors retain their full efficacy over time. An example of this delivery method is provided in FIG. 4 which shows an intervertebral disc 40 having tears 44a and 44b in annulus fibrosis 42. The composition (not shown) contained in the pump 46 is delivered to the tissue adjacent to tears 44a and 44b through a catheter 48.

Figure 4:
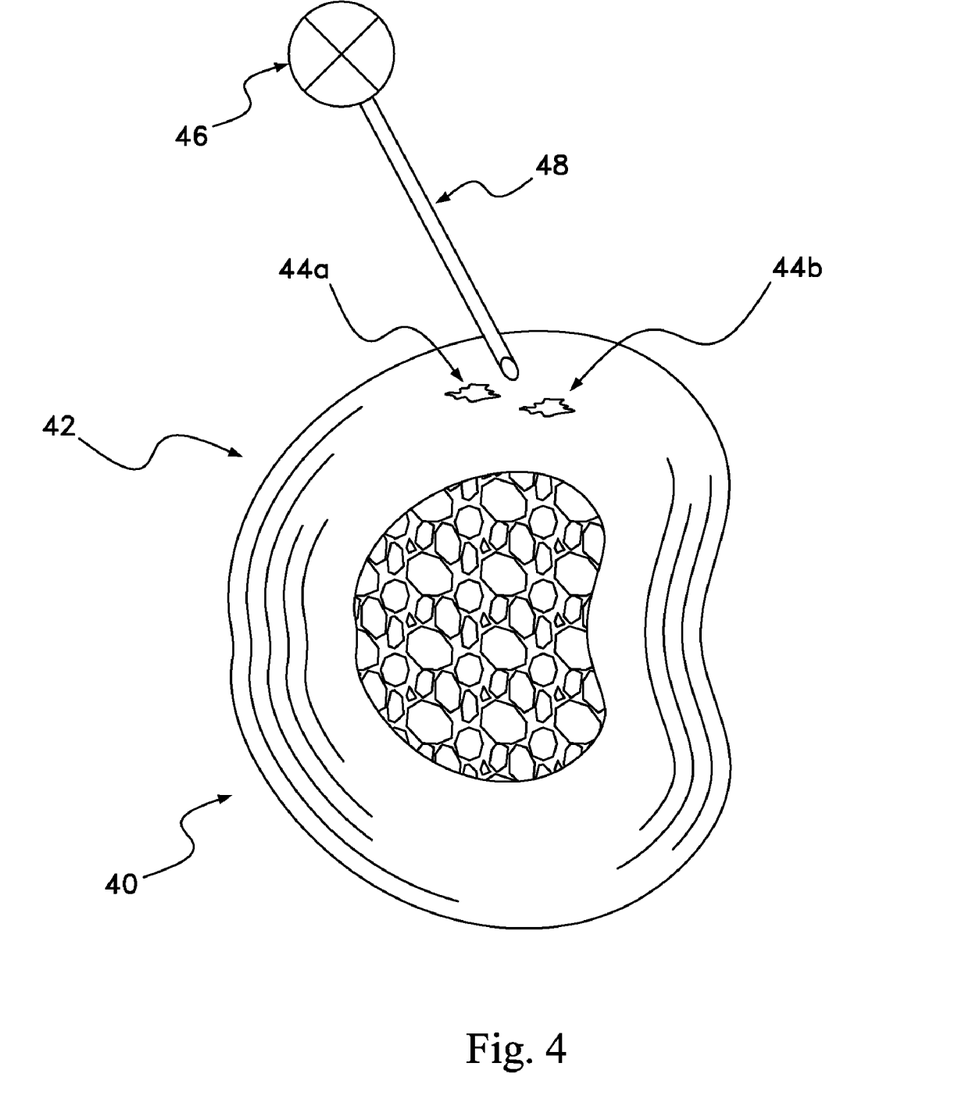

One example of a suitable pump is the SynchroMed® (Medtronic, Minneapolis, Minn.) pump. The therapeutic agent is pumped from the pump chamber and into the catheter, which will direct the therapeutic agent to the target site, i.e., into the tissue adjacent to the defect 44a, 44b. The rate of delivery of the therapeutic agent is controlled by a microprocessor. This allows the pump to be used to deliver similar or different amounts of the therapeutic agent continuously, at specific times, or at set intervals between deliveries, thereby controlling the release rates to correspond with the desired targeted release rates.

Additional designs which may be adapted to be employed in the method of the present invention are provided, for example, in United States Patent Applications, such as U.S. 2002/0082583 (a pre-programmable implantable apparatus with a feedback regulated delivery method), U.S. 2004/0106914 (a micro-reservoir osmotic release system for controlled release of chemicals), U.S. 2004/0064088 (a small, light-weight device for delivering liquid medication), U.S. 2004/0082908 (an implantable microminiature infusion device), U.S. 2004/0098113 (an implantable ceramic valve pump assembly), and U.S. 2004/0065615 (an implantable infusion pump with a collapsible fluid chamber). Alzet® osmotic pumps (Durect Corporation, Cupertino, Calif.) are also available in a variety of sizes, pumping rates and durations that may be suitable for use in the method of the present invention. One of ordinary skill in the art will readily understand that other types or configurations of pumps and fluid delivery devices (i.e., catheters) may be adapted for use in the instant invention, and that the above are simply exemplary and by no means exhaustive.

Potential drug delivery devices that may be suitable for use with the pump include, but are not limited to, those devices found in U.S. Pat. No. 6,551,290 (Elsberry, et al.), which describes a medical catheter for targeted, specific drug delivery; U.S. Pat. No. 6,571,125 (Thompson), which describes an implantable medical device for controllably releasing a biologically-active agent; U.S. Pat. No. 6,594,880 (Elsberry), which describes an intraparenchymal infusion catheter system for delivering therapeutic agents to selected sites in an organism; and U.S. Pat. No. 5,752,930 (Rise, et al.), which describes an implantable catheter for infusing equal volumes of agents to spaced sites.

In another embodiment, a method of treating a defect in a soft tissue comprises disposing a carrier matrix in or near the defect, providing a pump capable of delivering an effective amount of a fibrosis inducing factor, and fluidly connecting the pump to the carrier matrix. These methods are particularly suitable for treatment of ruptured intervertebral discs. The carrier matrix ensures that the nucleus pulposus is contained within the annulus fibrosus and provides a scaffold for the fibrous tissue to close the tear. Preferably, between approximately 0.001 to 60 mg of the fibrosis inducing factor is delivered over a 1 to 3 month period. In some embodiments, the amount of the fibrosis inducing factor may range between about 1 and 5 mg for the patient with small defects. Alternatively, the amount of the fibrosis inducing factor delivered to the patient may range from about 20 to 40 mg in cases with more serious defects.

Figure 5:
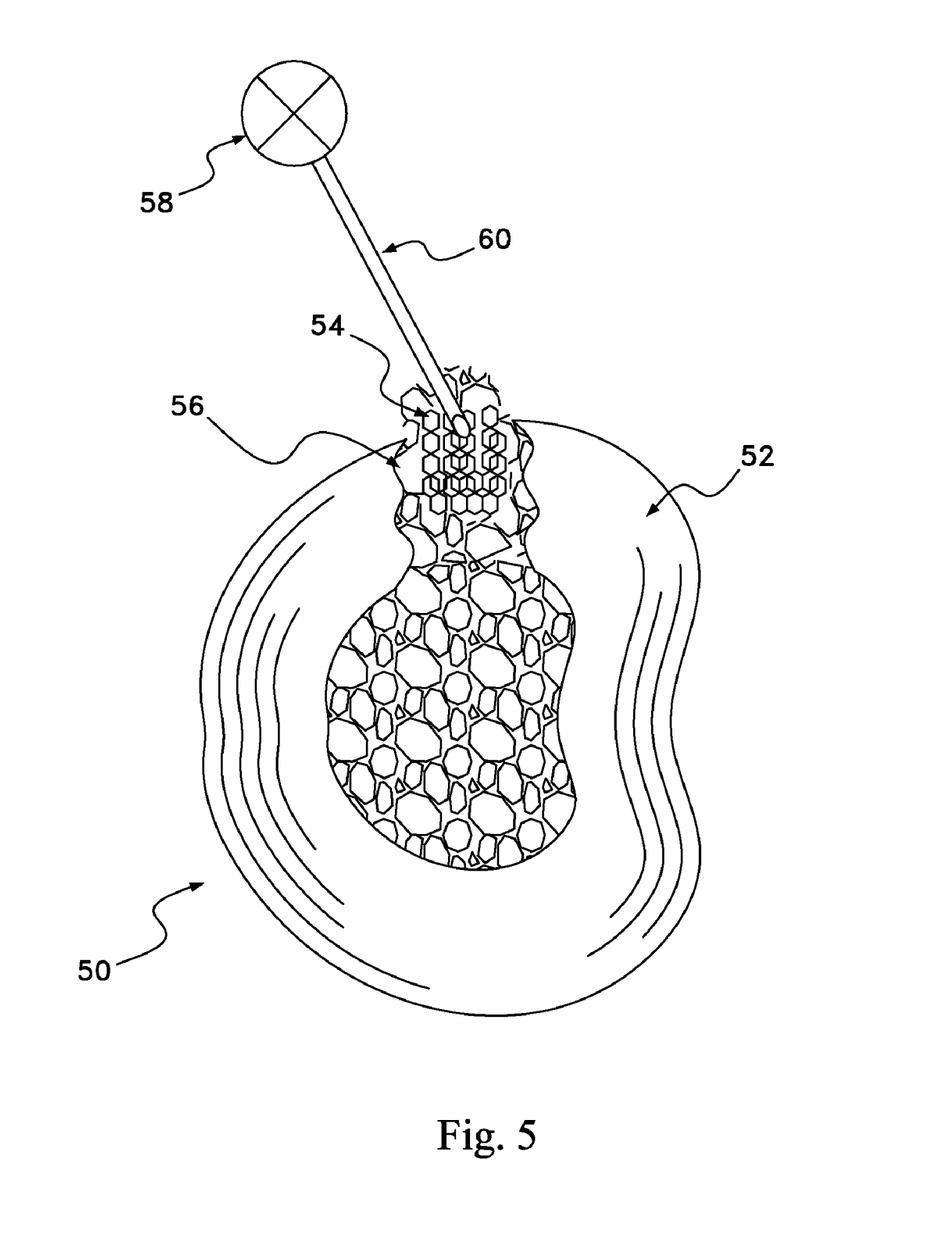
FIG. 5 illustrates administering a composition according to another embodiment.

FIG. 5 illustrates this embodiment. First, a carrier matrix 54 is disposed near or in the tear 56 in tissue 52. In some embodiments, the matrix may have a relatively low viscosity ranging between about 1 and 20,000 centipoise, and preferably between about 1 and 1000 centipoise to facilitate matrix adhesion to or entry into the healthy tissue. Alternatively, the matrix may have a high viscosity to minimize loss of material from the implant site. In such embodiment, the viscosity range is between about 20,000 and 5,000,000 centipoise. In some embodiments, the matrix may set up or partially set up upon delivery.

Although, FIG. 5 shows a completely ruptured annulus fibrosus, the method of this embodiment is suitable for prevention of the rupture. Accordingly, the carrier matrix may be positioned in or near a defect in the annulus fibrosus similar to the defects 44a and 44b shown in FIG. 4 to strengthen the annulus fibrosus in order to prevent complete rupture. The carrier matrix 54 may be delivered to the defect 56 by any minimally invasive method known in the art, such as an injection through a cannula or a catheter. A pump 58 is provided that is fluidly connected to the carrier matrix 56 via a catheter 60. The pump 58 delivers the fibrosis inducing factor to the matrix 54 via catheter 60.

The present invention may be used at different stages of disc degeneration. The methods described above are suitable to halt or reverse weakening of the annulus fibrosis at the early stages of the disease. For example, injecting a bulging disc with the fibrosis inducing factor may strengthen the annulus fibrous resulting in resorption of the hernia.

Signs of weakness in the annulus fibrosis can be observed by any known imaging techniques. In some cases, the imaging protocol may include the administration of a contrasting agent, as for example, in a discography. Such procedure commonly entail an initial application of local anesthetic (i.e. lidocaine, etc.) to the skin and/or subcutaneous tissue of the injection site. Then, an injection of 1-2 cc of contrast media (i.e. Omnipaque™ or similar) via a 22 gage spinal needle is placed percutaneously, often in a posteriolateral orientation. Needle placement into the nucleus pulposus and the path of the media is visualized under fluoroscopic imaging, and the degree of disc degeneration as well as the presence of annular fissures is readily apparent. Other known imaging methods such as X-Ray, MRI or CAT scans are also suitable.

The methods above are also suitable to treat discs in the later stages of degeneration such as ruptured discs. FIG. 5 shows one method of treatment for discs in later stages of disease, i.e. ruptured discs. Additionally, the present invention may be used to promote formation of fibrosis tissue in the nuclear region after removal of the nucleus pulposus to stabilize the disc and to minimize motion and compression of the disc that may cause pain. The disc may be removed by a surgical procedure such as discectomy or through chemical treatment such as presented in U.S. application Ser. No. 10/634,798 entitled "Methods and Devices for the Treatment of Intervertebral Discs," incorporated herein by reference. A higher dose of the fibrosis inducing factor and longer treatment regimen may be required in order to fully replenish the tissue within the disc following the procedure.

Figure 6A:
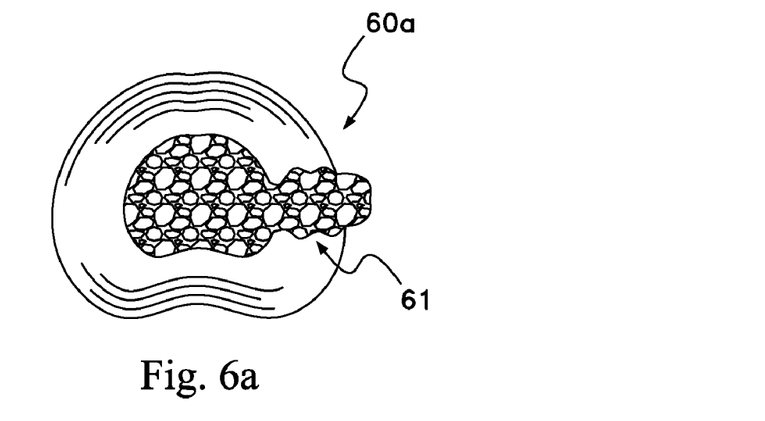
FIG. 6a, FIG. 6b and FIG. 6c illustrate one suitable use of the disclosed methods.
Figure 6B:
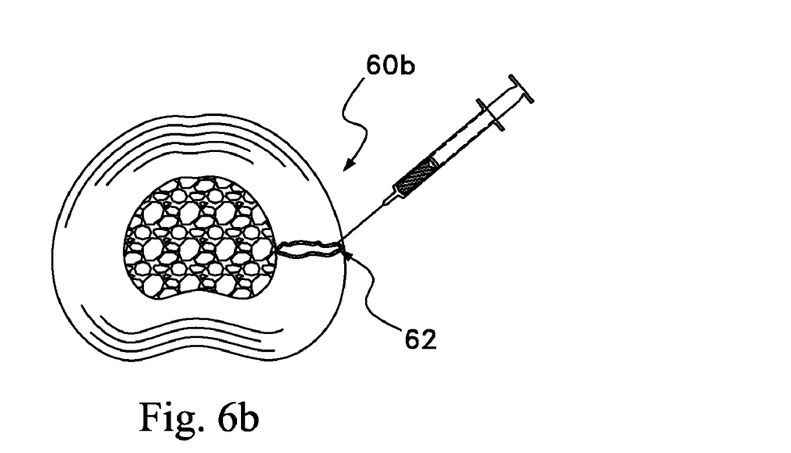
Figure 6C:
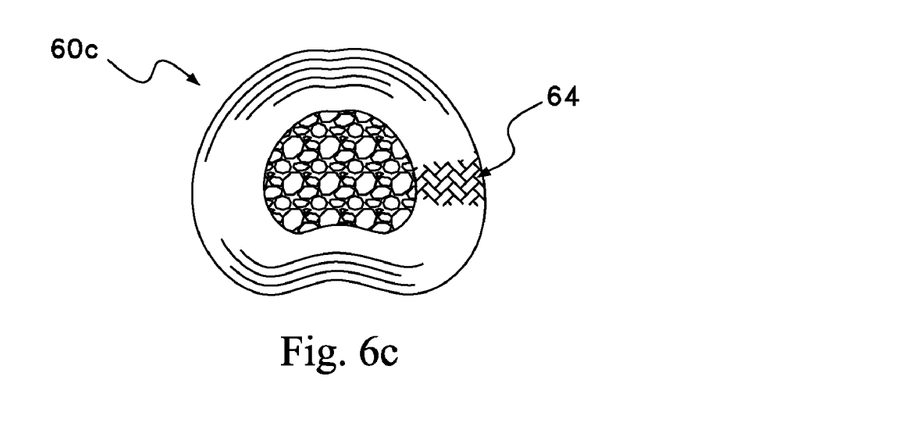

Finally the methods disclosed above can be utilized to help the body scar over the hole created by the surgeon when removing, or at least partially removing, disc nucleus fragments. For example, FIG. 6a shows a rupture 61 in a disc 60a. FIG. 6b illustrates injection of the fibrosis inducing factor into tissue adjacent to defect 62, i.e. a hole created by the surgeon after removal of nucleus pulposus fragment. Finally, FIG. 6c shows a disc 60c with a defect 62 closed by fibrous tissue 64.

Although the methods and compositions of the present invention were illustrated in reference to degenerative disease of intervertebral discs, these methods are also suitable for treatment of degenerative diseases associated with other soft tissues. The methods and compositions described above are suitable to treat injuries that include, but are not limited to, facet capsule tears, ligamentous tears, tendon tears, muscles tears, meniscus tears, shoulder rotator cuffs injuries, anterior cruciate ligaments tears, achilles tendon tears, injuries to wrist tendons, and spinal ligament tears among others.

Figure 7:
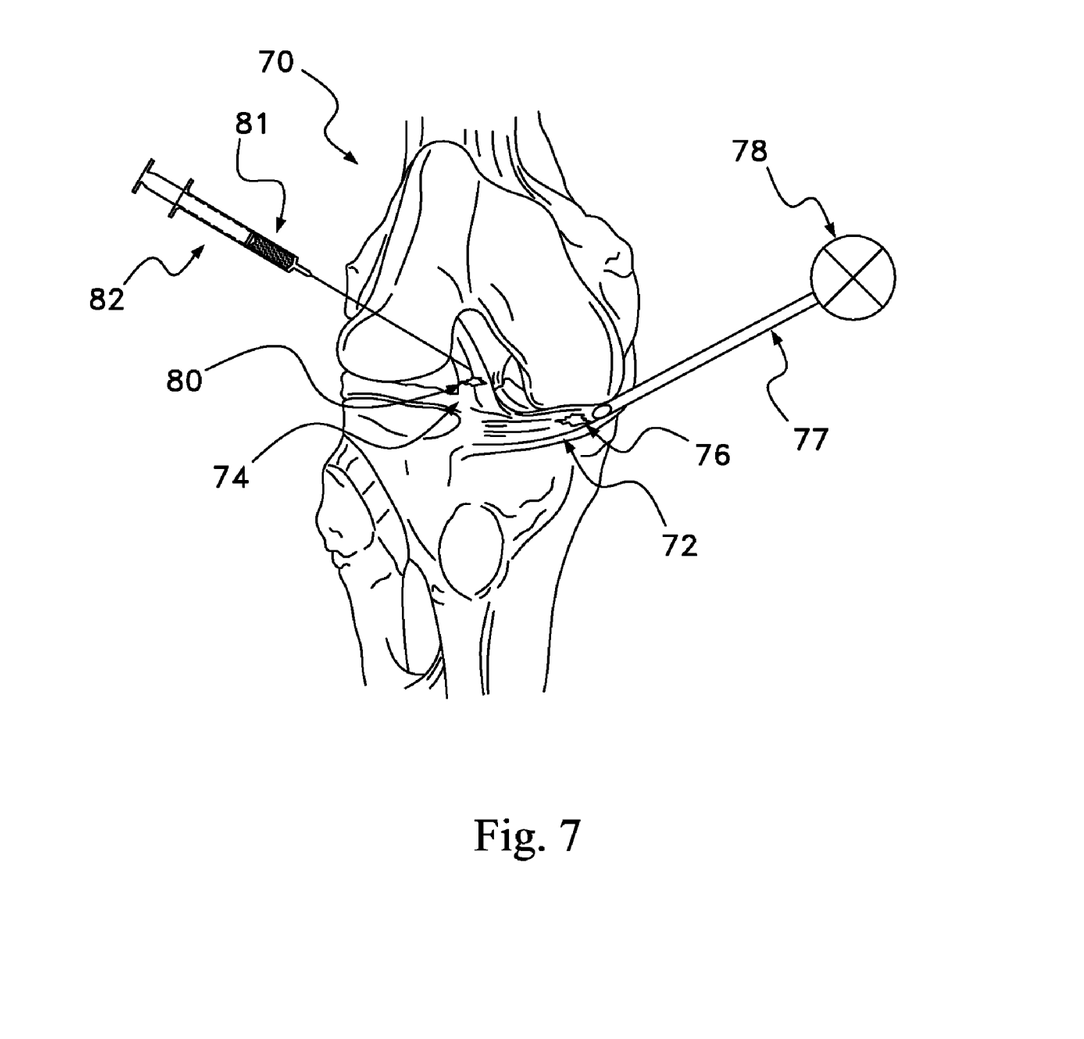
FIG. 7 illustrates a method of treatment of a medial meniscus anterior and cruciate ligament of a knee joint.

For example, FIG. 7 shows a right knee joint 70. A defect 76 in a medial meniscus 72 may be repaired by delivering a fibrosis inducing factor (not shown) contained in the pump 78 to the tissue adjacent to the defect 76 through a catheter 77. Similarly, fibrosis inducing factor 81 may be injected from a syringe 82 into the tissue of an anterior cruciate ligament 74 adjacent to a defect 80 to repair the defect 80.

All publications cited in the specification, both patent publications and non-patent publications, are indicative of the level of skill of those skilled in the art to which this invention pertains. All of these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A composition for treatment of a tear in a soft tissue comprising a fibrosis inducing factor comprising TGFβ1 and a carrier slurry comprising a biocompatible fluid and a polymer in a ratio of about 1:2 to 1:5, the polymer having a viscosity of about 20,000 to about 5,000,000 centipoise, wherein the composition is injectable directly into the soft tissue adjacent to the tear and wherein the concentration of the fibrosis inducing factor is between about 0.1 and about 10 mg/ml and the fibrosis inducing factor is encapsulated in microspheres.

2. The composition of claim 1, wherein the soft tissue is selected from the group consisting of muscles, tendons, ligaments, fibrous tissues, fibrocartilage, connective tissue, cartilage, fat, blood vessels, nerves, and synovial tissues.

3. The composition of claim 1, wherein the soft tissue is annulus fibrosus tissue.

4. The composition of claim 1, wherein the biocompatible fluid is selected from the group consisting of water, saline solution, buffered solutions, concentrated plasma, blood, blood with thrombin, bone marrow aspirant, glycerol or combinations thereof.

5. The composition of claim 1, wherein the polymer is a natural polymer selected from the group consisting of collagen, gelatin, chitosan, carboxymethylcellulose, hyaluronic acid, elastin, silk, glycosaminoglycans, polysaccharides, proteoglycans, peptides, polypeptides, and combinations thereof.

6. The composition of claim 1, wherein the polymer is a synthetic polymer is selected from the group consisting of poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, vinylpyrrolidone, polyvinyl alcohol (PVA), PVA-g-PLGA, PEGT-PBT copolymer (polyactive), methacrylates, poly(N-isopropylacrylamide), PEO- PPO- PEO (pluronics), PEO- PPO- P AA copolymers, PLGA-PEO-PLGA, polyphosphoesters, polyanhydrides, polyester-anhydrides, polyurethane-esters, polyphosphazines, polycaprolactones, poly trimethylene carbonates, polydioxanones, polyamide-esters, polyketals, polyacetals, glycosaminoglycans, polyethylene-vinyl acetates, silicones, polyurethanes, polypropylene fumarates, polydesaminotyrosine carbonates, polydesaminotyrosine arylates, polydesaminotyrosine ester carbonates, polydesaminotyrosine ester arylates, polyethylene oxides, polyorthocarbonates, polycarbonates, or copolymers or physical blends thereof or combinations thereof.

7. The composition of claim 1, wherein the carrier provides sustained release of the fibrosis inducing factor.

8. The composition of claim 1, wherein the diameter of microspheres ranges between about 1 and 250 microns.

9. The composition of claim 1, wherein the fibrosis inducing factor is encapsulated in biodegradable pellets.

10. The composition of claim 1, wherein the concentration of the fibrosis inducing factor is between about 2 and about 6 mg/ml.

11. The composition of claim 1, wherein the fibrosis inducing factor is released over about 60 days at a rate of about 0.5 mg per day.

* * * * *